United States Patent [19]

Schapira et al.

[11] Patent Number: 5,716,902
[45] Date of Patent: Feb. 10, 1998

[54] HERBICIDAL TREATMENT AND COMPOSITIONS BASED ON AMINOTRIAZOLE AND 1,2,4-TRIAZIN-5-ONES

[75] Inventors: Joseph Schapira; Isabelle Maillet, both of Paris; Gérard Sergent, Levallois Perret, all of France

[73] Assignee: CFPI ACRO, Gennevilliers, France

[21] Appl. No.: 651,296

[22] Filed: May 22, 1996

[30] Foreign Application Priority Data

May 24, 1995 [FR] France ................... 95 06242

[51] Int. Cl.$^6$ ................... A01N 43/653; A01N 43/707
[52] U.S. Cl. ................... 504/134
[58] Field of Search ................... 504/134

[56] References Cited

U.S. PATENT DOCUMENTS

| | | | |
|---|---|---|---|
| 3,909,234 | 9/1975 | Faust et al. | 71/93 |
| 4,032,324 | 6/1977 | Faust et al. | 71/93 |
| 5,441,923 | 8/1995 | Tocker | 504/125 |

FOREIGN PATENT DOCUMENTS 18 15 145  12/1968  Germany .

Primary Examiner—S. Mark Clardy
Attorney, Agent, or Firm—Keck, Mahin & Cate

[57] ABSTRACT

Herbicidal compositions based on aminotriazole comprising, besides the usual constituents, adjuvants and/or supports, on the one hand aminotriazole and on the other hand a proportion by weight with respect to the aminotriazole from about 1 to about 14.3%, preferably from 2.5 to 4% and, still more preferably, of about 3% of at least one triazinone of formula

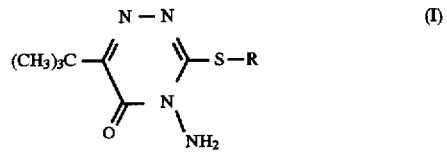

wherein R represents a linear or branched alkyl radical comprising from 1 to 4 carbon atoms, the proportion of triazinone in a given composition being selected taking into account the fact that the said composition should provide per hectare an amount of triazinone lower than 300 g, preferably lower than 200 g and still more preferably lower than or equal to 100 g.

Herbicidal treatment implementing these compositions.

29 Claims, No Drawings

HERBICIDAL TREATMENT AND COMPOSITIONS BASED ON AMINOTRIAZOLE AND 1,2,4-TRIAZIN-5-ONES

The invention relates to an improved herbicidal treatment and to herbicidal compositions based on aminotriazole.

It also relates to a process using the said compositions.

Herbicidal treatments and compositions are already known wherein the active substance is consisting of aminotriazole, or 1H-1,2,4-triazol-3-amine presenting the formula

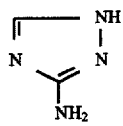

which is a well-known herbicide, widely used in selective or total weed-control and which gives full satisfaction; aminotriazole is generally used at rates of about 2000 à 5000 g/ha.

Other herbicidal treatments and compositions are known wherein the active substance is consisting of certain triazinones consisting of 4-amino-6-(1,1-dimethylethyl)-3-(alkylthio)-1,2,4-triazin-5(4H)-ones represented by the formula:

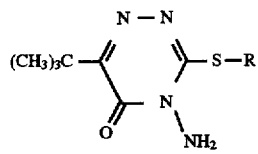

wherein R represents a linear or branched alkyl radical comprising from 1 to 4 carbon atoms; these triazinones are well-known herbicides; they are generally used at rates from 500 to 900 g/ha.

It has also been proposed, in the German patent application DOS 18 15 145, to carry out treatments providing total weed-control on pathways, squares, railroad tracks and non-crop areas, using total weed-killers comprising a combination of two active materials respectively consisting of aminotriazole and of one 4-amino-1,2,4-triazine-one present in proportions from 4:1 to 1:4, i.e. from 25 to 400% of triazinone with respect to the aminotriazole, the said combination of active materials being used at rates from 5 to 50 kg/ha; each one of the two products constituting the said combination of active materials is consequently used at rates at which it fully develops its herbicidal effect.

The Applicants, in the course of their researches to optimize the uses of aminotriazole, were able to find that it is possible, surprisingly and unexpectedly, to potentiate the herbicidal effects of aminotriazole as soon as that compound, used at usual rates per hectare, is put in the presence, when contacting the plant species to be destroyed, of a very low proportion of certain of the representatives of the abovesaid family of triazinones, the said proportion corresponding to an amount per hectare of these triazinones lower than about 300 g, amount at which the said triazinones would develop, if they were used alone, a herbicidal activity absolutely insufficient, or even negligible to zero, the said representatives being more especially those which are known under the names metribuzine and ethiozine for which R corresponds respectively to a methyl and to an ethyl radical in formula (I).

By way of consequence, the herbicidal treatment based on aminotriazole according to the invention is characterized by the fact that there are applied to the plant species to be destroyed, simultaneously or separately from one another, on the one hand an amount from 500 to 5000 g/ha of aminotriazole and, on the other hand an amount lower than 300 g/ha, preferably lower than 200 g/ha and still more preferably lower than or equal to 100 g/ha of at least one triazinone of formula (I) in such a way that the aminotriazole is in the presence of the triazinone when coming into contact with the plant species to be destroyed, the proportion by weight of triazinone used with respect to the amount of aminotriazole used being, provided that the abovesaid rates per hectare are observed, from about 1 to about 14.3%, preferably from 2.5 to 4% and, still more preferably, of about 3%, the herbicidal compositions based on aminotriazole according to the invention are characterized by the fact that they contain, besides the usual constituents, adjuvants and/or supports, on the one hand aminotriazole and on the other hand a proportion by weight with respect to the aminotriazole from about 1 to about 14.3%, preferably from 2.5 to 4% and, still more preferably, of about 3% of at least one triazinone of formula (I), the proportion of triazinone in a given composition being selected taking into account the fact that the said composition should provide per hectare an amount of triazinone lower than 300 g, preferably lower than 200 g and still more preferably lower than or equal to 100 g.

Due to the potentiation of the herbicidal effects of the aminotriazole which is obtained due to the invention, a composition according to the invention which provides per hectare about 1000 g of aminotriazole is substantially as efficient as an amount of about 3000 g/ha of aminotriazole used alone.

According to an advantageous embodiment, in the herbicidal treatment and in the herbicidal compositions according to the invention the aminotriazole and the triazinone are used in a weight ratio from 100/1 to 7/1, preferably from 40/1 to 25/1 and still more preferably of 33/1.

According to another advantageous embodiment, the herbicidal treatment according to the invention is characterized by the fact that there are applied by spraying on the plant species to be destroyed, simultaneously or separately from one another, two herbicidal compositions respectively based on aminotriazole as far as the first is concerned and on at least one triazinone of formula (I) as far as the second is concerned, each one in amounts sufficient to provide per hectare of the land under cultivation from 500 to 5000 g and preferably from 1000 to 3000 g of aminotriazole as far as the first herbicidal composition is concerned, and from 5 to 300 g and preferably from 12.5 to 200 g of at least one triazinone as far as the second herbicidal composition is concerned, the weight ratio between aminotriazole and triazinone being from 100/1 to 7/1, preferably from 40/1 to 25/1 and still more preferably of 33/1, due to which there is achieved, in situ on the plants, the formation of the composition according to the invention.

From a more general point of view, the herbicidal compositions based on aminotriazole according to the invention may contain usual adjuvants such as solid or liquid supports as well as the surfactive agents normally used in agriculture.

The said compositions can also comprise at least one of the agents of the group comprising activating agents, protecting agents, adhesives, thickeners, thixotropic agents, penetration agents, stabilizing agents, sequestering agents, water retention agents, dyes, surface agents, corrosion inhibitors, diluents and others.

It is also possible to add to the said compositions other active materials, especially at least one of those of the group comprising the herbicides, the fungicides, the insecticides, the growth regulators and the development regulators of plants, as well as the pesticides, being underlined that, within the frame of the present invention, pesticide means any chemical product used in agriculture and different from herbicides, fungicides, insecticides and growth regulators, as for instance bactericides and antidotes of herbicides.

More generally, the compositions according to the invention can comprise the solid or liquid additives used in the normal formulation techniques.

The herbicidal compositions according to the invention may be ready-to-use or may be extemporaneously prepared by mixing of two herbicidal compositions respectively based on aminotriazole and on at least one triazinone of formula (I).

The process implementing the compositions according to the invention is characterized by the fact that the said compositions are applied by spraying, on the plant species to be destroyed, in pre-emergence or post-emergence, in an amount sufficient to provide per hectare of land of cultivation:

from 500 to 5000 g and preferably from 1000 to 3000 g of aminotriazole, and from 5 to 300 g and preferably from 12.5 to 200 g of at least one triazinone, the weight ratio between the aminotriazole and the triazinone being from 100/1 to 7/1, preferably from 40/1 to 25/1 and still more preferably of 33/1.

Due to the invention, it becomes possible to control, on the cultivated plants selected from among vineyards, orchards, olive trees, rubber trees, ornamental trees and shrubs, on fallow-land, on forest trees or non-crop lands, in selective or total weed-control, preferably by application in post-emergence, a great variety of annual or perennial weeds, mono- or dicotyledoneous and especially those of the group comprising Agropyron sp., *Allium vineale, Arrhenatherum elatius, Avena fatua, Cirsium arvense, Daucus carota, Epilobium tetragonum, Erigeron canadensis, Erodium cicutarium,* Geranium sp., *Poa annua, Rumex acetosa, Senecio vulgaris,* Stellaria sp., Veronica sp.

The invention will still be better understood with the help of the following non-limiting examples wherein advantageous embodiments of the invention are disclosed.

EXAMPLE 1

In view of a biological test in green-house, two compositions according to the invention were prepared, the constitutions of which appear from Table I.

TABLE I

|  | aminotriazole (g/l) | metribuzine (g/l) |
|---|---|---|
| Composition 1 | 120 | 4.5 |
| Composition 2 | 120 | 3 |

These compositions are prepared starting:
on the one hand, from an aqueous solution of technical aminotriazole identified under CA 1558 and comprising 240 g/l of active substance,
on the other hand, from a wettable powder comprising 35% of metribuzine marketed under the trademark SENCORAL® 35.

For example, in order to obtain one liter of composition 1, 12.86 g de SENCORAL® 35 are added to half a liter of CA 1558 as well as an amount of water sufficient to provide 1 liter of composition.

Composition 2 is prepared according to the same process selecting the proportions in order to obtain the desired concentrations.

Compositions 1 and 2 are applied by spraying respectively at the rate of 10 l/ha and 15 l/ha, which corresponds, as far as composition 1 is concerned, to 1200 g/ha of aminotriazole and 45 g/ha of metribuzine and, as far as composition 2 is concerned, to 1800 g/ha of aminotriazole and 45 g/ha of metribuzine; the plant species to be destroyed are *Ambrosia artemisiifolia, Daucus carota, Festuca elatior* and *Sorgum vulgare* cultivated in green-house in pots and then treated at the 3 to 4 leaf stage.

Each of the two active materials are also applied independently from one another at the rates corresponding to the two compositions 1 and 2.

28 days after the treatment, the herbicidal effect of these compositions on the treated species is observed.

Hereafter the expression "Expected results" means the percentage of destruction of the plants treated calculated starting from, on the one hand, the effect of destruction (X) obtained when applying aminotriazole alone and, on the other hand, the effect of destruction (Y) obtained when applying the triazinone alone, the value of the "expected results" being calculated using the formula:

$$\text{Expected result} = X + Y - \frac{XY}{100} \quad (A)$$

in which X and Y represent the observed percentages of destruction of the treated plants with respect to an untreated control for which the destruction of the plants is considered as being equal to 0%.

The expression "Results as obtained" means the actually observed percentage of destruction of the treated plants with respect to an untreated control for which the destruction of the plants is considered as being equal to 0%.

The results obtained after application of aminotriazole and triazinone alone, those expected and calculated for the compositions 1 and 2 using the abovesaid formula (A) and, finally, those actually observed for these compositions are collected in Table II.

TABLE II

|  | Results as obtained (%) after individual spraying of the constituents of the compositions | | | Expected results (%) for compositions | | Results as obtained (%) for compositions | |
|---|---|---|---|---|---|---|---|
|  |  |  |  | 1 | 2 | 1 | 2 |
| Aminotriazole (g/ha) | 1200 | 1800 | 0 | 1200 | 1800 | 1200 | 1800 |
| Metribuzine (g/ha) | 0 | 0 | 45 | 45 | 45 | 45 | 45 |
| Ambrosia artemisiifolia | 65 | 70 | 10 | 68.5 | 73.0 | 80 | 92 |
| Daucus carota | 50 | 55 | 10 | 55.0 | 59.5 | 87 | 95 |
| Festuca elatior | 55 | 65 | 15 | 61.8 | 70.3 | 82 | 90 |
| Sorgum vulgare | — | 30 | 10 | — | 37.0 | — | 60 |

The results collected in the above Table show the negligible herbicidal effect of the triazinone when used alone; they clearly show the potentiation or doping effect of the triazinone on the aminotriazole, being understood that there occurs a potentiation or a synergistic effect each time when the results obtained by the use of compositions 1 and 2 are higher than the expected results.

EXAMPLE 2

In view of a biological test in green-house, four compositions denoted 3 to 6 are prepared, the constitutions of which appear from Table III.

TABLE III

|  | aminotriazole (g/l) | metribuzine (g/l) |
|---|---|---|
| Composition 3 | 60 | 2.25 |
| Composition 4 | 60 | 4.5 |
| Composition 5 | 120 | 2.25 |
| Composition 6 | 120 | 4.5 |

These compositions are prepared using the same process as in example 1.

Each of the compositions 3 to 6 is applied at the rate of 8 l/ha, which corresponds, as far as compositions 3 and 4 are concerned, to 480 g/ha of aminotriazole and respectively to 18 and 36 g/ha of metribuzine and, as far as compositions 5 and 6 are concerned, to 960 g/ha of aminotriazole and respectively to 18 and 36 g/ha of metribuzine; the plants to be destroyed are *Chenopodium album*, *Raphanus raphanistrum*, *Solanum nigrum* and *Lolium multiflorum* cultivated in green-house in pots and then treated at the 3 to 4 leaf stage.

Each one of the two active materials comprised by each of the compositions 3 to 6 is also independently from the other applied at the rates which correspond to those of the said compositions.

28 days later, there is observed in each case the herbicidal effect on the studied species.

The results obtained after application of the aminotriazole and of the triazinone alone, those expected and calculated using the abovesaid formula (A) for the compositions 3 to 6 and, lastly, those actually observed in connection with the said compositions are collected in Table IV.

TABLE IV

|  | Results as obtained (%) after individual spraying of the constituents of compositions | | | | Expected results (%) for compositions | | | | Results as obtained (%) for compositions | | | |
|---|---|---|---|---|---|---|---|---|---|---|---|---|
|  |  |  |  |  | 3 | 4 | 5 | 6 | 3 | 4 | 5 | 6 |
| Aminotriazole (g/ha) | 480 | 960 | 0 | 0 | 480 | 460 | 960 | 960 | 480 | 480 | 960 | 960 |
| Metribuzine (g/ha) | 0 | 0 | 18 | 36 | 18 | 36 | 18 | 36 | 18 | 36 | 18 | 36 |
| *Chenopodium album* | 15 | 20 | 0 | 20 | 15,0 | 32,0 | 20,0 | 36,0 | 70 | 100 | 75 | 100 |
| *Raphanus raphanistrum* | 30 | 30 | 20 | 30 | 44,0 | 51,0 | 44,0 | 51,0 | 100 | 100 | 100 | 100 |
| *Solanum nigrum* | 20 | 30 | 0 | 0 | 20,0 | 20,0 | 30,0 | 30,0 | — | 50 | 80 | 80 |
| *Lolium multiflorum* | 30 | 35 | 0 | 0 | 30,0 | 30,0 | 35,0 | 35,0 | 50 | 60 | 65 | 65 |

Here again, the potentiation or doping effect of the herbicidal effect of aminotriazole by the triazinone clearly appears from the results collected in Table IV.

EXAMPLE 3

In view of a biological test in green-house, a composition according to the invention, denoted 7, whose constitution appears from Table V, is prepared.

TABLE V

|  | aminotriazole (g/l) | metribuzine (g/l) |
|---|---|---|
| Composition 7 | 192 | 10.5 |

The abovesaid composition is prepared using the same process as in example 1.

Composition 7 is applied at the date T and at the rate of 5 l/ha, which corresponds to 960 g/ha of aminotriazole and to 52.5 g/ha of metribuzine; the plant species to be destroyed are *Raphanus raphanistrum* cultivated in green-house in pots and then treated at the 3 to 4 leaf stage.

Independently from one another, each one of the two active materials comprised by composition 7 is also applied at the rate corresponding the said composition 7.

After durations equal to T+14 days, T+21 days and T+28 days, the herbicidal effect is observed in each case on the treated specie.

The results obtained after application of aminotriazole and of the triazinone alone, those expected and calculated using the abovesaid formula (A) for composition 7 and, finally, those actually observed for the said composition are collected in Table VI.

TABLE VI

|  | Results as obtained (%) after individual spraying of the constituents of the composition | | Expected results (%) for the composition | Results as obtained (%) for the composition |
|---|---|---|---|---|
| Aminotriazole (g/ha) | 960 | 0 | 960 | 960 |
| Metribuzine (g/ha) | 0 | 52.5 | 52.5 | 52.5 |

TABLE VI-continued

|  | Results as obtained (%) after individual spraying of the constituents of the composition | | Expected results (%) for the composition | Results as obtained (%) for the composition |
|---|---|---|---|---|
| T + 14 days | 30 | 20 | 44.0 | 80 |
| T + 21 days | 50 | 10 | 55.0 | 100 |

TABLE VI-continued

|  | Results as obtained (%) after individual spraying of the constituents of the composition | Expected results (%) for the composition | Results as obtained (%) for the composition |
| --- | --- | --- | --- |
| T + 28 days | 30 | 45 | 61.5 | 100 |

The results collected in the abovesaid Table show that the potentiation or doping effect on aminotriazole by the triazinone may appear early, i.e. 14 days after the date of treatment.

EXAMPLE 4

Example 4 reports the results of four biological tests, A, B, C and D, carried out on vineyard cultivated on field in agricultural plots. The tests, whose conditions are indicated in Table VII, are carried out according to a randomized block design with two replicates and untreated control included. The surface of the elementary plots is equal to 40 m².

TABLE VII

| Test No. | A | B | C | D |
| --- | --- | --- | --- | --- |
| Location | 30-Pouzilhac France | 84-Valras France | 81-Amarens France | 49-Brissac-Quincé France |
| Vine plant | Grenache noir | Carignan | Cabernet Sauvignon | Cabernet franc |
| Period of treatment | beginning of March | middle of March | middle of March | beginning of March |
| Stage of development at the moment of treatment according to the Eichhorn-Lorenz scale | 03 | 03 | 01 | 03 |
| Temperature (°C.) |  |  |  |  |
| at the moment of treatment | 19 | 16 | 13 | 17 |
| minimal | 10 | 10 | 04 | 06 |
| maximal | 20 | 20 | 13 | 17 |

In the abovesaid tests, the composition which was used is the composition according to the invention denoted whose constitution results from Table VIII.

TABLE VIII

|  | aminotriazole (g/l) | metribuzine (g/l) |
| --- | --- | --- |
| Composition 8 | 5.76 | 0.12 |

Composition 8 is obtained starting from:
on the one hand, a powder denoted CA27 and containing 100% by weight of aminotriazole,
on the other hand, a wettable powder containing 70% by weight of metribuzine and marketed under the trademark SENCORAL®.

For example, in order to obtain one liter of composition 8, 5.76 g of CA27 are diluted in 10 to 20 ml of water; 0.17 g of SENCORAL are added as well as an amount of water sufficient to make one liter of composition.

Two other compositions respectively denoted 9 and 10 are also used, these compositions containing only aminotriazole respectively at the rate of 5.76 g/l and 7.2 g/l; they are obtained starting from the powder CA27.

The three compositions are applied at the rate of 500 l/ha on the plant species to be destroyed, which corresponds:
as far as powder 8 is concerned, to 2880 g/ha of aminotriazole and to 60 g/ha of metribuzine,
as far as powders 9 and 10 are concerned, respectively to 2880 g/ha and to 3600 g/ha of aminotriazole alone.

One month later, the herbicidal effect of these compositions on the species treated is recorded. The results as obtained are expressed in percentage of destruction of the treated plants with respect to an untreated control for which the destruction of the plants is considered to be equal to 0%.

The results of the tests A, B, C and D are recorded respectively in Tables IX, X, XI and XII.

TABLE IX (these results are the average value of two replicates)

| | Results obtained (%) for the compositions | | |
| --- | --- | --- | --- |
|  | 8 | 9 | 10 |
| Aminotriazole (g/ha) | 2880 | 2880 | 3600 |
| Metribuzine (g/ha) | 60 | 0 | 0 |
| Chondrilla juncea | 100 | 85 | 100 |
| Erodium cicutarium | 68 | 18 | 45 |
| Geranlum molle | 100 | 63 | 100 |
| Stellaria media | 100 | 75 | 100 |
| Tordylium maximum | 100 | 50 | 100 |

TABLE X (these results are the average value of two replicates)

| | Results obtained (%) for the compositions | | |
| --- | --- | --- | --- |
|  | 8 | 9 | 10 |
| Aminotriazole (g/ha) | 2880 | 2880 | 3600 |
| Metribuzine (g/ha) | 60 | 0 | 0 |
| Cardamine hirsuta | 100 | 65 | 75 |
| Crepis species | 95 | 75 | 85 |

TABLE XI (these results are the average value of two replicates)

| | Results obtained (%) for the compositions | | |
| --- | --- | --- | --- |
|  | 8 | 9 | 10 |
| Aminotriazole (g/ha) | 2880 | 2880 | 3600 |
| Metribuzine (g/ha) | 60 | 0 | 0 |
| Calepina irregularis | 78 | 43 | 50 |
| Crepis sancta | 75 | 45 | 63 |
| Erodium cicutarium | 60 | 28 | 40 |
| Sonchus oleraceus | 93 | 45 | 75 |
| Veronica persica | 99 | 42 | 55 |

TABLE XII (these results are the average value of two replicates)

| | Results obtained (%) for the compositions | | |
| --- | --- | --- | --- |
|  | 8 | 9 | 10 |
| Aminotriazole (g/ha) | 2880 | 2880 | 3600 |
| Metribuzine (g/ha) | 60 | 0 | 0 |

TABLE XII-continued (these results are the average value of two replicates)

| | Results obtained (%) for the compositions | | |
|---|---|---|---|
| | 8 | 9 | 10 |
| Cirsium arvense | 80 | 60 | 79 |
| Erodium cicutarium | 97 | 78 | 98 |

The examination of the results recorded in Tables IX, X, XI and XII permits to establish the fact that:

on the one hand, for a given amount of aminotriazole applied per hectare, the addition of triazinone to the aminotriazole permits the obtention of an efficiency clearly higher than that of aminotriazole used alone, the increase of efficiency varying from 20 to 60% depending from the weed species under consideration, on the other hand, the results obtained using aminotriazole doped by triazinone are not obtained when using aminotriazole alone even at a rate which is 1.25 times higher.

From a more general point of view, the results of the tests carried out as well in green-house as in field show the potentiation of the aminotriazole when using a small proportion of triazinone.

The aminotriazole being thus optimised, it becomes possible:

to get a better level of efficiency using the same amount of aminotriazole, for an expected effect, to reduce the amount of aminotriazole, providing thus a lower cost and a better respect of the environment.

We claim:

1. Herbicidal treatment based on aminotriazole comprising applying to the plant species to be destroyed, simultaneously or separately from one another, on the one hand an amount from 500 to 5000 g/ha of aminotriazole and, on the other hand an amount lower than 300 g/ha of at least one triazinone of formula:

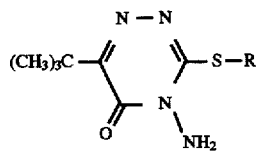

wherein R represents a linear or branched alkyl radical comprising from 1 to 4 carbon atoms, in such a way that the aminotriazole is in the presence of the triazinone when coming into contact with the plant species to be destroyed, the proportion by weight of triazinone used with respect to the amount of aminotriazole used being, provided that the abovesaid rates per hectare are observed, from 1 to 14.3%.

2. Herbicidal treatment according to claim 1, wherein the amount of the at least one triazinone is lower than 200 g/ha.

3. Herbicidal treatment according to claim 1, wherein the amount of the at least one triazinone is lower than or equal to 100 g/ha.

4. Herbicidal treatment according to claim 1, wherein the proportion by weight of triazinone used with respect to the amount of aminotriazole used is, provided that the abovesaid rates per hectare are observed, from 2.5 to 4%.

5. Herbicidal treatment according to claim 1, wherein the proportion by weight of triazinone used with respect to the amount of aminotriazole used is, provided that the abovesaid rates per hectare are observed, of 3%.

6. Herbicidal treatment according to claim 1, wherein aminotriazole and triazinone are used in a weight ratio from 100/1 to 7/1.

7. Herbicidal treatment according to claim 1, wherein aminotriazole and triazinone are used in a weight ratio from 40/1 to 25/1.

8. Herbicidal treatment according to claim 1, wherein aminotriazole and triazinone are used in a weight ratio of 33/1.

9. Herbicidal treatment based on aminotriazole according to claim 1, comprising applying by spraying on the plant species to be destroyed, simultaneously or separately from one another, two herbicidal compositions respectively based on aminotriazole as far as the first is concerned and on at least one triazinone of formula (I) as far as the second is concerned, each one in amounts sufficient to provide per hectare of the land under cultivation from 500 to 5000 g of aminotriazole as far as the first herbicidal composition is concerned, and from 5 to 300 g of at least one triazinone as far as the second herbicidal composition is concerned, the weight ratio between aminotriazole and triazinone being from 100/1 to 7/1, due to which there is achieved, in situ on the plants, the formation of the composition comprising the aminotriazole and the triazinone.

10. Herbicidal treatment according to claim 1, comprising applying by spraying on the plant species to be destroyed, simultaneously or separately from one another, two herbicidal compositions respectively based on aminotriazole as far as the first is concerned and on at least one triazinone of formula (I) as far as the second is concerned, each one in amounts sufficient to provide per hectare of the land under cultivation from 1000 to 3000 g of aminotriazole as far as the first herbicidal composition is concerned, and from 12.5 to 200 g of at least one triazinone as far as the second herbicidal composition is concerned, the weight ratio between aminotriazole and triazinone being from 100/1 to 7/1, due to which there is achieved, in situ on the plants, the formation of the composition comprising the aminotriazole and the triazinone.

11. Herbicidal treatment according to claim 1, wherein the weight ratio between aminotriazole and triazinone is from 40/1 to 25/1.

12. Herbicidal treatment according to claim 1, wherein the weight ratio between aminotriazole and triazinone is of 33/1.

13. Herbicidal compositions based on aminotriazole comprising, besides the usual constituents, adjuvants and/or supports, on the one hand aminotriazole and on the other hand a proportion by weight with respect to the aminotriazole from 1 to 14.3% of at least one triazinone of formula

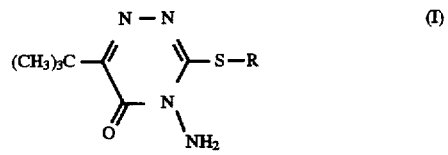

wherein R represents a linear or branched alkyl radical comprising from 1 to 4 carbon atoms, the proportion of triazinone in a given composition being selected taking into account the fact that the said composition provides per hectare an amount of triazinone lower than 300 g.

14. Herbicidal compositions according to claim 13, wherein the proportion by weight of the at least one triazinone with respect to the aminotriazole is from 2.5 to 4%.

15. Herbicidal compositions according to claim 13, wherein the proportion by weight of the at least one triazinone with respect to the aminotriazole is of 3%.

16. Herbicidal compositions according to claim 13, wherein the proportion of triazinone in a given composition is selected taking into account the fact that the said composition provides per hectare an amount of triazinone lower than 200 g.

17. Herbicidal compositions according to claim 13, wherein the proportion of triazinone in a given composition is selected taking into account the fact that the said composition provides per hectare an amount of triazinone lower than or equal to 100 g.

18. Herbicidal compositions according to claim 13, comprising aminotriazole and triazinone in a weight ratio from 100/1 to 7/1.

19. Herbicidal compositions according to claim 13, comprising aminotriazole and triazinone in a weight ratio from 40/1 to 25/1.

20. Herbicidal compositions according to claim 13, comprising aminotriazole and triazinone in a weight ratio of 33/1.

21. Herbicidal compositions according to claim 13, comprising conventional agricultural adjuvants, solid or liquid supports, and/or surfactants.

22. Herbicidal compositions according to claim 13, comprising at least one of the agents of the group consisting of activating agents, protecting agents, adhesives, thickeners, thixotropic agents, penetration agents, stabilizing agents, sequestering agents, water retention agents, dyes, surface agents, corrosion inhibitors, and diluents.

23. Herbicidal compositions according to claim 13, comprising at least another active material of the group consisting of the herbicides, the fungicides, the insecticides, the growth regulators, the development regulators of plants, and the pesticides.

24. Herbicidal compositions according to claim 13, wherein the triazinone of formula (I) is metribuzin.

25. Herbicidal compositions according to claim 13, wherein the triazinone of formula (I) is ethiozin.

26. Process implementing the compositions according to claim 17, comprising applying said compositions by spraying, on the plant species to be destroyed, in pre-emergence or post-emergence, in an amount sufficient to provide per hectare of land of cultivation:

from 500 to 5000 g of aminotriazole, and from 5 to 300 g of at least one triazinone, the weight ratio between aminotriazole and triazinone being from 100/1 to 7/1.

27. Process according to claim 26, comprising applying said compositions by spraying, on the plant species to be destroyed, in pre-emergence or post-emergence, in an amount sufficient to provide per hectare of land of cultivation:

from 1000 to 3000 g of aminotriazole, and from 12.5 to 200 g of at least one triazinone, the weight ratio between aminotriazole and triazinone being from 100/1 to 7/1.

28. Process according to claim 26, wherein the weight ratio between aminotriazole and triazinone is from 40/1 to 25/1.

29. Process according to claim 26, wherein the weight ratio between aminotriazole and triazinone is of 33/1.

* * * * *

UNITED STATES PATENT AND TRADEMARK OFFICE
CERTIFICATE OF CORRECTION

PATENT NO. : 5,716,902
DATED : February 10, 1998
INVENTOR(S) : Joseph SCHAPIRA et al.

It is certified that error appears in the above-identified patent and that said Letters Patent is hereby corrected as shown below:

On the title page, item [73]:

Item [73] change "CFPI ACRO" to --CFPI AGRO--.

Signed and Sealed this

Twenty-second Day of June, 1999

Attest:

Q. TODD DICKINSON

*Attesting Officer*      *Acting Commissioner of Patents and Trademarks*